(12) United States Patent
Bates et al.

(10) Patent No.: US 7,927,295 B2
(45) Date of Patent: Apr. 19, 2011

(54) DEVICE AND METHOD FOR COMPRESSING WOUNDS

(75) Inventors: James S. Bates, Sparta, NJ (US); John P. Budris, Cheshire, CT (US)

(73) Assignee: Datascope Investment Corp., Mahwah, NJ (US)

( * ) Notice: Subject to any disclaimer, the term of this patent is extended or adjusted under 35 U.S.C. 154(b) by 0 days.

(21) Appl. No.: 12/488,073

(22) Filed: Jun. 19, 2009

(65) Prior Publication Data

US 2009/0318952 A1  Dec. 24, 2009

Related U.S. Application Data

(63) Continuation of application No. 11/891,912, filed on Aug. 13, 2007, now abandoned, which is a continuation of application No. 11/043,350, filed on Jan. 26, 2005, now abandoned, which is a continuation of application No. 10/397,785, filed on Mar. 26, 2003, now abandoned.

(60) Provisional application No. 60/368,013, filed on Mar. 27, 2002.

(51) Int. Cl.
*A61F 5/00* (2006.01)
*A61F 13/00* (2006.01)
*A61B 17/12* (2006.01)

(52) U.S. Cl. ............. 602/13; 602/53; 606/201; 606/202

(58) Field of Classification Search .................. 602/13, 602/53; 606/201–204, 191
See application file for complete search history.

(56) References Cited

U.S. PATENT DOCUMENTS

| | | | |
|---|---|---|---|
| 3,171,410 A | 3/1965 | Towle, Jr. et al. | |
| 3,874,387 A | 4/1975 | Barbieri | |
| 4,202,331 A | 5/1980 | Yale | |
| 4,224,945 A | 9/1980 | Cohen | |
| 4,300,542 A | 11/1981 | Baron | |
| 4,436,089 A | 3/1984 | Schmid | |
| 4,480,638 A | 11/1984 | Schmid | |
| 4,829,994 A | 5/1989 | Kurth | |
| 4,957,105 A | 9/1990 | Kurth | |
| 5,234,459 A * | 8/1993 | Lee | 606/203 |

(Continued)

FOREIGN PATENT DOCUMENTS

JP  5-277125  10/1993

(Continued)

OTHER PUBLICATIONS

Office Action from corresponding Japanese Application 2003-579674. (English translation).

(Continued)

*Primary Examiner* — Kim M Lewis
(74) *Attorney, Agent, or Firm* — Lerner, David, Littenberg, Krumholz & Mentlik, LLP

(57) ABSTRACT

A dressing for applying compression to a wound in a patient includes a bladder having a non-deformable end wall and a deformable membrane. The dressing may include a flexible web having an adhesive layer on one side thereof for securing the dressing to the patient so as to hold the bladder against the patient's skin. Upon inflation, the deformable membrane projects towards the patient's skin and exerts pressure on the wound to reduce the flow of blood from the wound.

17 Claims, 6 Drawing Sheets

U.S. PATENT DOCUMENTS

| | | | |
|---|---|---|---|
| 5,263,965 A | | 11/1993 | Roth |
| 5,307,811 A | | 5/1994 | Sigwart et al. |
| 5,376,067 A | | 12/1994 | Daneshvar |
| 5,389,066 A | * | 2/1995 | Rhame, Jr. .................. 602/74 |
| 5,464,420 A | | 11/1995 | Hori et al. |
| 5,486,194 A | | 1/1996 | Kawasaki et al. |
| 5,507,721 A | | 4/1996 | Shippert |
| 5,643,315 A | | 7/1997 | Daneshvar |
| 5,690,610 A | | 11/1997 | Ito et al. |
| 5,792,173 A | * | 8/1998 | Breen et al. .................. 606/201 |
| 5,799,650 A | | 9/1998 | Harris |
| 5,968,072 A | | 10/1999 | Hite et al. |
| 5,997,564 A | | 12/1999 | Shehata et al. |
| 6,264,673 B1 | | 7/2001 | Egnelov et al. |
| 6,503,266 B1 | * | 1/2003 | Sjogren et al. .................. 606/201 |
| 2002/0082541 A1 | | 6/2002 | Chan |

FOREIGN PATENT DOCUMENTS

| | | |
|---|---|---|
| JP | 7-047073 A | 2/1995 |
| JP | 2000-515773 | 11/2000 |
| WO | 90/11744 A1 | 10/1990 |
| WO | 97/02783 | 1/1997 |

OTHER PUBLICATIONS

Supplementary European Search Report, EP 03745616, dated Jun. 23, 2009.

* cited by examiner

DEVICE AND METHOD FOR COMPRESSING WOUNDS

CROSS-REFERENCE TO RELATED APPLICATIONS

This is a continuation of application Ser. No. 11/891,912 filed Aug. 13, 2007 now abandoned, which is a continuation of application Ser. No. 11/043,350 filed Jan. 26, 2005 now abandoned, which is a continuation of application Ser. No. 10/397,785 filed Mar. 26, 2003 now abandoned, which claims the benefit of the filing date of U.S. Provisional Application No. 60/368,013 filed Mar. 27, 2002, the disclosures of which are hereby incorporated by reference herein.

BACKGROUND OF THE INVENTION

The present invention relates generally to a device and method for compressing a wound in a patient caused by any one of a number of medical procedures. In a particular embodiment, the present invention is directed to a device and method for compressing and sealing a puncture wound in a blood vessel of a patient caused by a medical procedure.

In certain medical procedures, such as cardiac catheterization, dilation and counterpulsation, a catheter or other device is inserted into an artery, most commonly by percutaneous methods, and then fed through the arterial tree to the site where needed, frequently, the region of the heart. The site usually selected for insertion is the groin because the femoral artery in that region is relatively easy to locate.

These procedures are normally initiated by insertion of an angiographic needle, followed by passing a guide wire through that needle into the artery. The needle is then removed, leaving the guide wire in place. Next, a sheath/dilator set is passed over the guide wire into the artery in order to enlarge the opening sufficiently to permit entry of the catheter or other device. The dilator is then removed, leaving the sheath or guide cannula in place. The catheter or other device can then be inserted through the cannula with full confidence that when it emerges from the distal end it will be within the lumen of the artery.

After a procedure, for example, counterpulsation, has been completed, the sheath must be removed and the wound closed. Often, this can be accomplished simply by the application of digital pressure, generally augmented by the use of a conventional pressure dressing, until hemostasis is achieved. Customarily, pressure must be applied for at least one half hour, and frequently for much longer than that. In addition, during this period the patient must be immobilized, lest movement interfere with the closing process. Because of the pressure required, the time during which it must be applied and the need for immobilization, the procedure is painful and uncomfortable. It also requires the prolonged personal attention of a health care professional. Finally, wound closures accomplished in this manner are prone to open unexpectedly long after closure appears to have been completed. Patients are therefore often required to maintain bedrest, oftentimes in the hospital, for 24 hours or longer.

In addition to the need for applied pressure to seal a puncture wound in an artery or blood vessel of a patient, there are other medical situations in which the application of pressure to a particular region of a patient's body is required. For example, there may be a requirement for pressure to stanch bleeding or reduce hematomas following biopsies, ambulatory dialysis, insertion of intravenous needles, emergency procedures and other such situations.

Although devices have been developed to address these situations, and particularly the difficulties associated with achieving hemostasis of an artery or blood vessel, these devices have met with various degrees of success and oftentimes create new difficulties. There therefore exists a need for a device for applying compression to wounds in patients which is inexpensive, effective, easy to use and comfortable for the patient, and which overcomes many of the drawbacks of the prior art devices.

SUMMARY OF THE INVENTION

The present invention addresses these needs.

One aspect of the present invention provides a dressing for applying compression to a wound in a patient. The dressing includes an inflatable bladder having a non-deformable end wall and a deformable membrane connected to the end wall so as to define an enclosed space therebetween. The bladder has a deflated condition in which the membrane is adjacent the end wall and an inflated condition in which the membrane is spaced from the end wall. Holding means are provided for holding the bladder against the skin of the patient in a position substantially overlying the wound without circumscribing the leg or torso of the patient.

The holding means may include a flexible web connected to the end wall of the bladder and projecting outwardly therefrom. The flexible web may extend radially outward in all directions from the bladder and may include a layer of adhesive on one surface for adhering the flexible web to the skin of the patient.

The bladder in the inflated condition may decrease in size in a direction away from the end wall. In preferred embodiments, the bladder in the inflated condition may have a frusto-conical or frusto-pyramidal shape.

The end wall may be formed from a rigid material, such as plastic, and may be transparent. The end wall may also be formed from the same material as the deformable membrane, and may be molded integrally with the deformable membrane.

Another aspect of the present invention provides a method of applying compression to a wound in a patient. The method includes providing a dressing including an inflatable bladder having a non-deformable end wall and a deformable membrane connected to the end wall so as to define an enclosed space therebetween; applying the dressing against the skin of the patient in a position substantially overlying the wound; inflating the bladder to an inflated condition, whereby the inflated bladder exerts pressure on the wound to reduce the flow of blood from the wound; and applying manual pressure to the dressing against the skin of the patient so as to achieve hemostasis of the wound.

The method may further include providing a flexible web connected to the end wall of the bladder, the flexible web having a layer of adhesive on one surface thereof, and adhering the flexible web to the patient's skin.

The bladder in the inflated condition may decrease in size in a direction away from the end wall. In preferred methods, the bladder in the inflated condition may have a frusto-conical or frusto-pyramidal shape.

The providing step may include providing the dressing such that the end wall and the deformable membrane are formed from the same material. The providing step may further include providing the dressing such that the end wall and the deformable membrane are molded integrally with one another.

Preferred dressings in accordance with the present invention and compression methods employing same reduce the time in which health care professionals must exert manual compression to a wound, while at the same time increasing patient mobility and comfort.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

Figure 1:
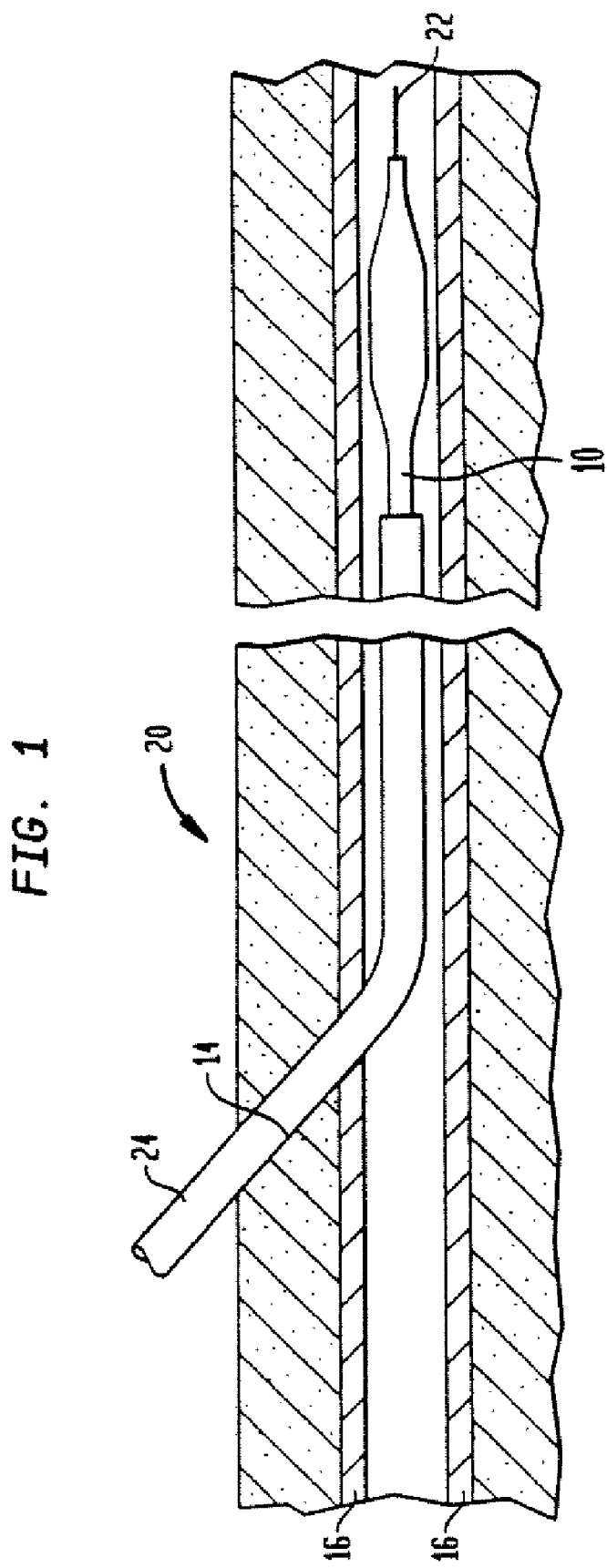
FIG. 1 is an enlarged, schematic, cross-sectional view of one type of insertion site, showing a balloon catheter having passed over a guide wire through a guide cannula into the femoral artery of the patient.

In certain procedures, for example, intra-aortic balloon pumping ("IABP"), percutaneous transluminal coronary angioplasty ("PTCA") and angiography, as best seen in FIG. 1, a catheter or other device 10 is inserted through a puncture wound 14 and into a blood vessel or artery 16, most frequently, the common femoral artery in the groin area of the patient's leg 20. Puncture wound 14 includes a tissue channel extending through a layer of tissue separating artery 16 from the patient's skin. Often, the insertion of device 10 is facilitated by passing the device over a guide wire 22 and through a guide cannula 24. When the procedure (e.g., counterpulsation) has been completed, the device (e.g., the catheter), the guide wire and the guide cannula must be removed and the puncture wound closed. Although puncture wounds of the sort made by percutaneous procedures will generally, after removal of all cannulas and catheters, be in the nature of slits, for ease of understanding, they are depicted in the drawings herein more as holes. The shape of the puncture wound, however, is not critical.

It should be understood that the subject invention is independent of the nature of the medical device being used to treat the patient. Accordingly, the term "catheter" is used herein in a very generic and broad way to include not only "catheters" in the strict sense, but any device that is inserted into the body.

Similarly, the subject invention is independent of whether a particular blood vessel is involved, and if so, which blood vessel. While it is anticipated that the femoral artery will be the most commonly used blood vessel for many percutaneous procedures, other arteries as well as veins might just as easily be involved.

Figure 2:
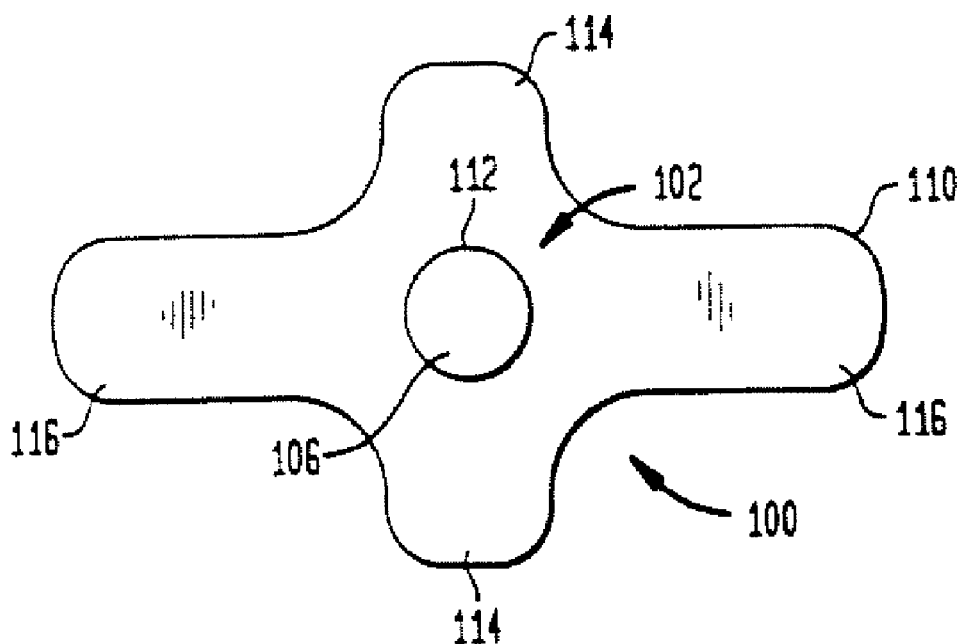
FIG. 2 is a bottom plan view of one embodiment of the compression dressing of the present invention showing the side that faces the puncture wound.
Figure 3:
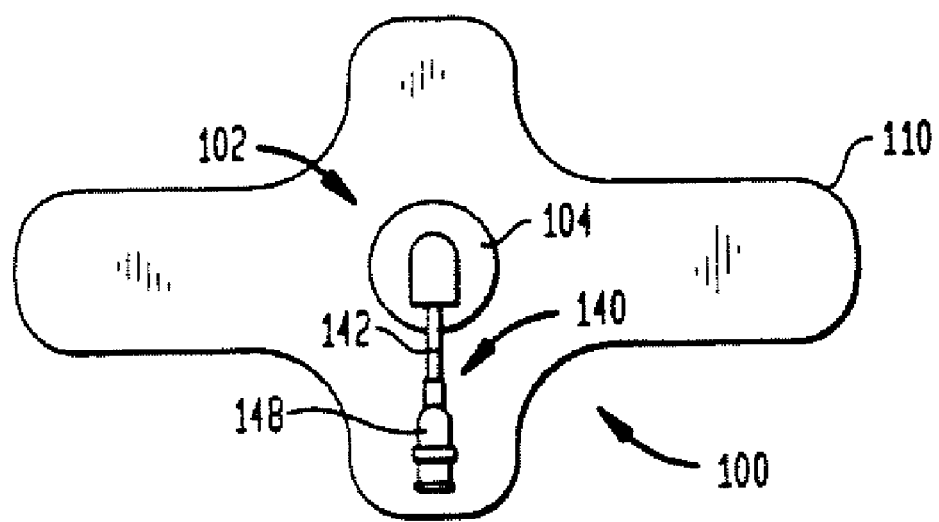
FIG. 3 is a top plan view of the compression dressing of FIG. 2.

A compression dressing 100 for use in sealing puncture wound 14 is shown in FIGS. 2 and 3. Dressing 100 includes an expandable bladder 102 having an end wall 104 and a lower membrane 106 enclosing an internal region 108. End wall 104 is formed from a material that will resist substantial deformation at the pressures to which bladder 102 is inflated during normal use. Thus, for example, end wall 104 may be formed from a rigid plastic material, a rigid metal or some other relatively rigid material. Preferably, end wall 104 is formed from a transparent plastic disc so that the inflation of bladder 102 and any leakage of blood from puncture wound 14 can be readily observed therethrough.

In contrast, membrane 106 is formed from a pliant, air-impermeable material such that membrane 106 will deform upon inflation of bladder 102. In one arrangement, membrane 106 may be formed from the same material as end wall 104. For example, in a one-piece molding operation, end wall 104 may be formed with a relatively thick cross-section such that it will not substantially deform at the pressures to which bladder 102 is inflated during use, and membrane 106 may be formed with a relatively thin cross-section such that it will readily deform upon inflation of bladder 102. Alternatively, end wall 104 and membrane 106 may be formed from different materials altogether.

Bladder 102 in the inflated condition may have any shape capable of exerting sufficient pressure on the patient's leg to occlude bleeding. In a preferred arrangement, however, membrane 106 has a shape such that the inflated bladder 102 will taper from a larger size to a smaller size in the direction toward the patient. For example, in the inflated state, bladder 102 may have the shape of an inverted pyramid or cone. Such shapes will concentrate the pressure exerted by compression dressing 100 on a localized region of the patient, desirably a region overlying the wounded artery. Bladder 102 in the inflated condition may alternatively have a frusto-pyramidal or frusto-conical shape, thereby avoiding any pain to the patient which may result from having the inflated point of bladder 102 forced against the patient's skin. Other shapes are also contemplated herein. Moreover, it will be appreciated that by varying the wall thickness and shape of membrane 106, various levels of force and conformity with the contour of the patient's skin may be achieved.

Membrane 106 may be treated with an anti-bacterial coating in order to minimize the occurrence of infections in puncture wound 14 resulting from the use of compression dressing 100. In addition, membrane 106 may be treated with any number of materials known to those skilled in the art to aid in the healing of puncture wound 14 or to reduce pain or complications.

Bladder 102 is secured to the lower surface of an attachment web 110. Web 110 is preferably formed from a flexible material which will readily conform to the contour of the patient's leg. Particularly preferred are materials that are permeable to air, such as woven fabrics and perforated plastic sheets. The attachment of bladder 102 to web 110 may be made by an adhesive; mechanical means, such as sewing or stapling; ultrasonic or solvent welding; and any other known techniques. In a preferred arrangement, the edges of bladder 102 are encased within one or more layers of adhesive as discussed below in connection with FIG. 9. An aperture 112 may be formed in web 110 in a region overlying end wall 104. Aperture 112 may enable substantially the entirety of bladder 102 to be seen through web 110 to assure proper placement and operation of compression dressing 100.

Web 110 may extend outwardly from bladder 102 in all directions so as to define a continuous region around bladder 102 by which dressing 100 may be attached to the patient's leg. However, web 110 need not extend outwardly from bladder 102 by equal amounts in all directions. Thus, as shown in FIG. 2, web 110 may include substantially perpendicular arms 114 and 116 which extend radially outwardly from bladder 102 by a greater extent than the remainder of web 110. Although FIG. 2 shows arms 114 as shorter than arms 116, that is not necessarily the case; arms 114 may be longer than arms 116 or arms 114 and 116 may have substantially the same length.

Figure 4:
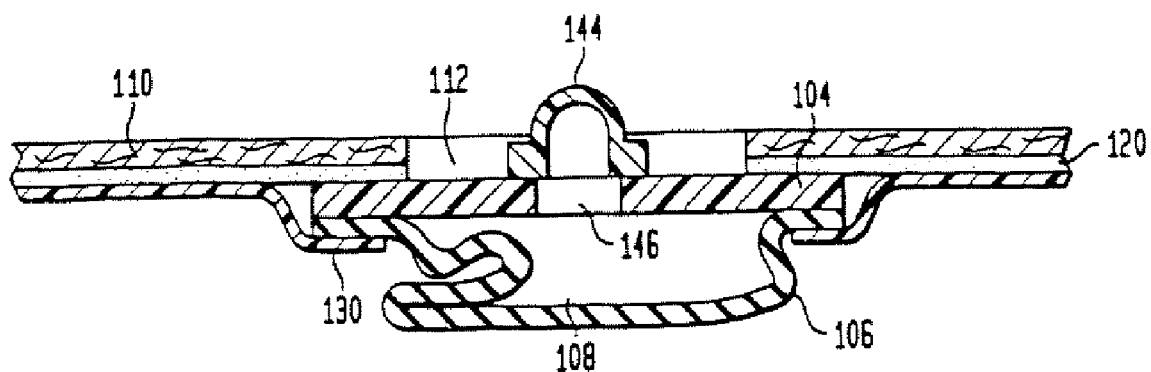
FIG. 4 is a cross-sectional view of the compression dressing taken along line 4-4 of FIG. 3 and showing the bladder in a deflated condition.
Figure 5:
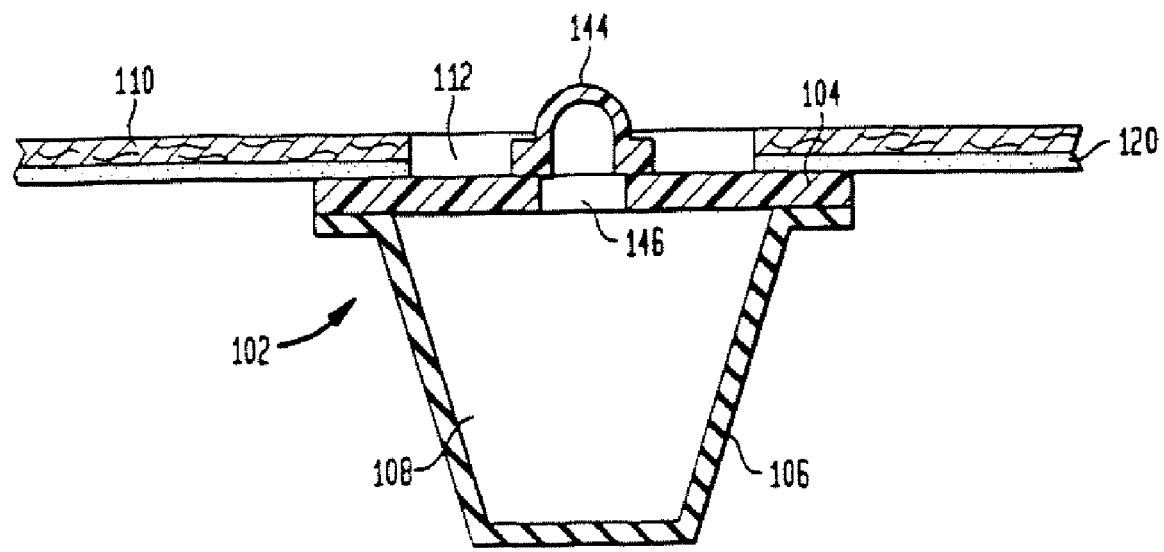
FIG. 5 is the same view as FIG. 4, but showing the bladder in an inflated condition.

The bottom surface of web 110 (i.e., the surface confronting the patient's skin) includes an adhesive layer 120 for adhering dressing 100 to the patient's skin in the region surrounding puncture wound 14. Thus, dressing 100 is adhered to the patient and does not require that arms 114 or 116 circumscribe the body of the patient, in particular the leg or torso of the patient. Adhesive layer 120 may entirely coat the bottom surface of web 110. Alternatively, adhesive layer 120 may be applied only in discrete regions of the bottom surface of web 110 such that the portion of web 110 adjacent bladder 102 is held tightly against the patient's skin. Moreover, as noted above, adhesive layer 120 may be used to adhere end wall 104 of bladder 102 to attachment web 110, such as shown in FIGS. 4 and 5. A removable protective sheet 130 may cover adhesive layer 120 during shipping and handling. As explained below, protective sheet 130 is removed from dressing 100 prior to its use.

A mechanism 140 for inflating bladder 102 is provided on the end wall 104 of the bladder. Mechanism 140 includes a tube 142 having one end connected to end wall 104 by a connector 144 and communicating with the interior of bladder 102 through an aperture 146 in end wall 104. A one-way valve assembly 148 is connected to the other end of tube 142. Any known inflation mechanism may be used to inflate bladder 102. One such inflation device is a squeeze bulb, such as squeeze bulb 150 shown in FIG. 6, which may be connected to mechanism 140 through valve assembly 148. Other inflation mechanisms include, but are not limited to, compressed air canisters, a centralized source of air distributed through the wall or ceiling, or a gas generated through a chemical reaction within bladder 102, such as by crushing chemical-containing vials, etc. Alternatively, bladder 102 may be inflated by a fluid, such as saline, in order to provide weight to the dressing and reduce the compressibility of the inflated bladder.

Figure 6:
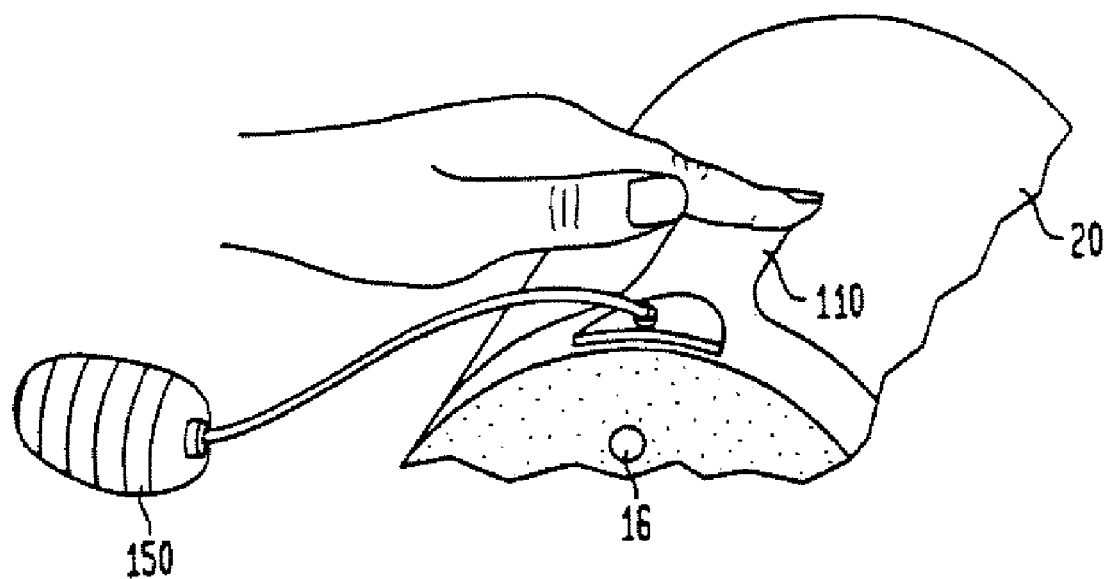
FIG. 6 is a perspective view showing the application of the compression dressing to a patient, the bladder of the compression dressing being in a deflated condition.
Figure 7:
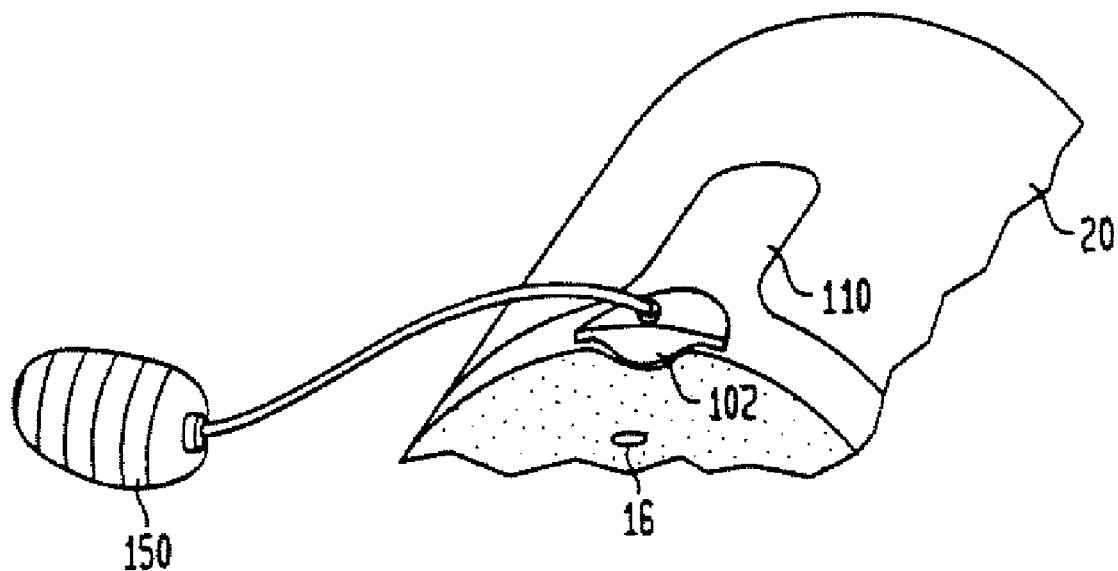
FIG. 7 is a perspective view showing the application of the compression dressing to a patient, the bladder of the compression dressing being in an inflated condition.
Figure 8:
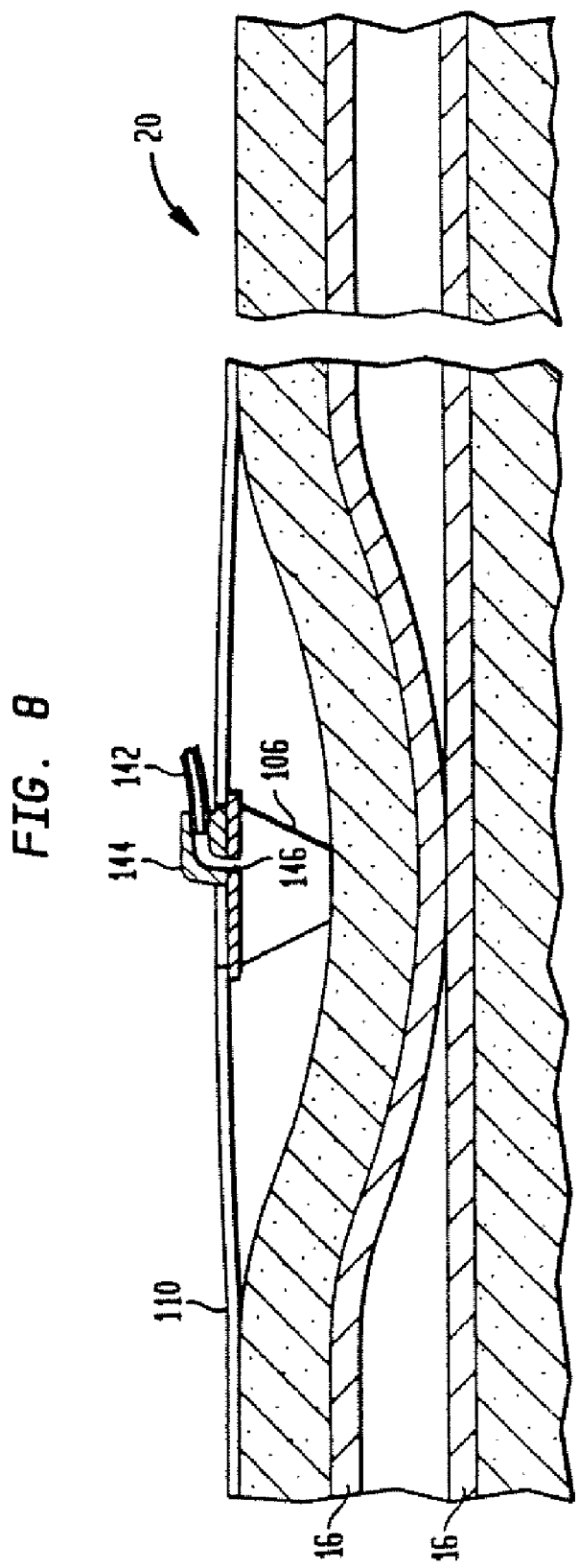
FIG. 8 is an enlarged, schematic, cross-sectional view showing the insertion site of FIG. 1 after the catheter, cannula and guide wire have been removed, and showing the use of the compression dressing to seal the puncture wound.

The application of compression dressing 100 to a patient and the operation thereof will now be described with particular reference to FIGS. 6-8. After protective sheet 130 has been removed and before bladder 102 is inflated, the dressing 100 is applied so that adhesive layer 120 contacts the skin of the patient, and so that bladder 102 is positioned over or just upstream of puncture wound 14. Squeeze bulb 150 or another inflation device may then be used to inflate bladder 102 to a desired pressure. Since end wall 104 resists deformation as bladder 102 is inflated, as the inflation material fills internal region 108 of bladder 102, membrane 106 will be pushed away from end wall 104 and toward the patient's skin. As this occurs, the adhesive layer 120 on web 110 holds bladder 102 in tight relationship against the skin of the patient. As a result, the inflation of bladder 102 causes the patient's skin and underlying tissue and artery to be compressed, thereby stanching the flow of blood through the tissue below.

Dressing 100 may be used with or without an initial period of manual compression. In that regard, manual compression may initially be applied to the wound site to achieve hemostasis before application of dressing 100. After hemostasis has been achieved, dressing 100 may be applied and bladder 102 inflated. Alternatively, manual compression may be performed directly over dressing 100 after its application to the patient but before it has been inflated. In a further variant, manual compression may be performed directly over dressing 100 subsequent to inflation of bladder 102. In this regard, membrane 106 may be formed with a shape which will facilitate the ease of applying this compression. In all of these methods, once manual compression has been completed, the inflated bladder 102 would continue to maintain pressure on the puncture wound to maintain hemostasis.

Figure 9:
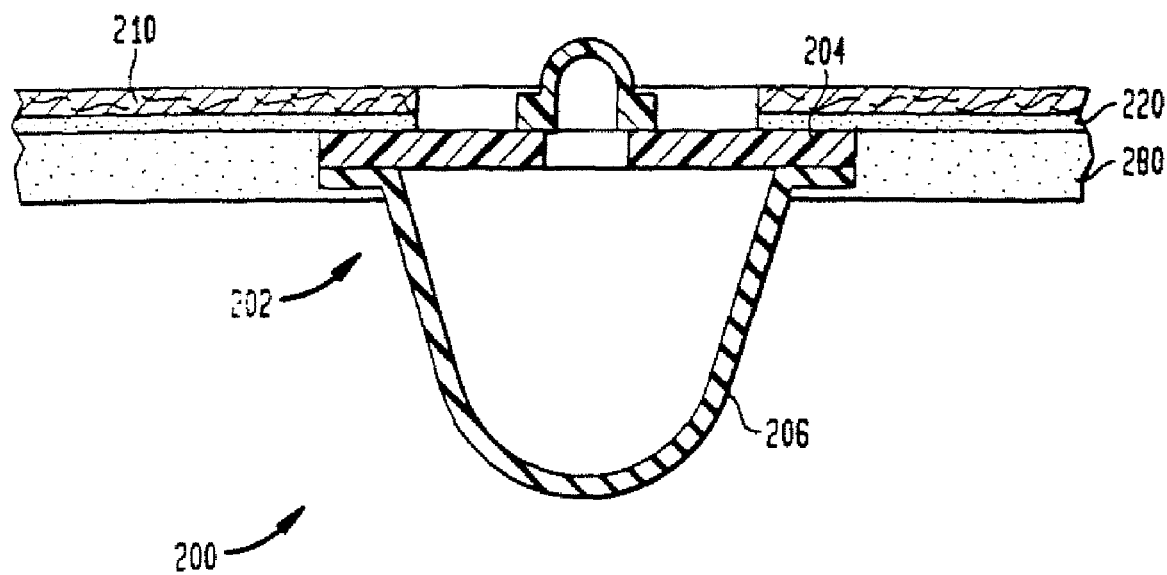
FIG. 9 is a cross-sectional view of a compression dressing in accordance with an alternate embodiment of the present invention, showing the bladder in an inflated condition.

An alternate embodiment of a dressing in accordance with the present invention is illustrated as dressing 200 in FIG. 9. Dressing 200 is substantially the same as dressing 100 described above, but differs in the shape of the deformable membrane and in the method of securing the bladder to the attachment web. Thus, dressing 200 includes a deformable membrane 206 which is more rounded than membrane 106, eliminating any sharp corners or edges which could cause discomfort for the patient. Also, dressing 200 includes a first layer of adhesive 220 which substantially coats one surface of attachment web 210 and adheres bladder 202 to the web, and a second layer of adhesive 280 which covers the peripheral edge of membrane 206 in the region in which the membrane is connected to end wall 204. With this arrangement, the outer edges of end wall 204 and membrane 206 are encased within adhesive so that no free edges are exposed to the patient's skin. It will be appreciated that the same effect can be achieved without adhesive layer 280 having the same outward extent as adhesive layer 220, or without adhesive layer 220 having the same outward extent as adhesive layer 280.

Variants of dressings 100 and 200 will be readily apparent to those skilled in the art. For example, rather than having the attachment web adhesively secured to the patient's skin, arms 116 of the web may be formed with sufficient length that they can extend around the patient's leg and connect to one another, such as by tying, clasps, hook and loop fasteners, etc. Alternatively, the bladder may be secured to a patient's leg by a belt, strap or other device positioned over or operatively connected to the end wall thereof.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as set forth in the appended claims.

The invention claimed is:

1. A dressing for applying compression to a wound in the groin of a patient, comprising:

an inflatable bladder having a non-deformable end wall and a deformable membrane connected to the end wall so as to define an enclosed space therebetween, the bladder having a deflated condition and an inflated condition; and holding means for holding the bladder against the skin of the patient in a position substantially overlying the wound without circumscribing the leg or torso of the patient.

2. The dressing as claimed in claim 1, wherein the holding means includes a flexible web connected to the end wall of the bladder and projecting outwardly therefrom.

3. The dressing as claimed in claim 2, wherein the flexible web extends radially outward in all directions from the bladder.

4. The dressing as claimed in claim 2, further comprising a layer of adhesive on one surface of the flexible web for adhering the flexible web to the skin of the patient.

5. The dressing as claimed in claim 1, wherein the bladder in the inflated condition decreases in size in a direction away from the end wall.

6. The dressing as claimed in claim 1, wherein the end wall is transparent.

7. The dressing as claimed in claim 1, wherein the end wall and the deformable membrane are formed from the same material.

8. The dressing as claimed in claim 7, wherein the end wall and the deformable membrane are molded integrally with one another.

9. A dressing for applying compression to a wound in a patient, comprising:
- a deformable membrane defining a cavity having an open end;
- a non-deformable member enclosing the open end so as to define an inflatable bladder having an enclosed space bounded by the deformable membrane and the non-deformable member, the bladder having a deflated condition and an inflated condition; and
- holding means for holding the bladder against the skin of the patient in a position substantially overlying the wound.

10. The dressing as claimed in claim 9, wherein the holding means includes a flexible web connected to the non-deformable member and projecting outwardly therefrom.

11. The dressing as claimed in claim 10, wherein the flexible web extends radially outward in all directions from the bladder.

12. The dressing as claimed in claim 10, further comprising a layer of adhesive on one surface of the flexible web for adhering the flexible web to the skin of the patient.

13. The dressing as claimed in claim 10, wherein the flexible web includes an aperture overlying the non-deformable member to enable the non-deformable member to be visible when the bladder is in the position substantially overlying the wound.

14. The dressing as claimed in claim 9, wherein the bladder in the inflated condition decreases in size in a direction away from the non-deformable member.

15. The dressing as claimed in claim 9, wherein the non-deformable member is transparent.

16. The dressing as claimed in claim 9, wherein the non-deformable member and the deformable membrane are formed from the same material.

17. The dressing as claimed in claim 16, wherein the non-deformable member and the deformable membrane are molded integrally with one another.

* * * * *